(12) United States Patent
Rantala

(10) Patent No.: US 8,126,525 B2
(45) Date of Patent: Feb. 28, 2012

(54) PROBE AND A METHOD FOR USE WITH A PROBE

(75) Inventor: Borje Rantala, Helsinki (FI)

(73) Assignee: GE Healthcare Finland Oy, Helsinki (FI)

( * ) Notice: Subject to any disclaimer, the term of this patent is extended or adjusted under 35 U.S.C. 154(b) by 1459 days.

(21) Appl. No.: 11/565,905

(22) Filed: Dec. 1, 2006

(65) Prior Publication Data

US 2007/0129616 A1    Jun. 7, 2007

(30) Foreign Application Priority Data

Dec. 2, 2005    (EP) ..................................... 05111626

(51) Int. Cl.
*A61B 5/1455*    (2006.01)
(52) U.S. Cl. ........................................ 600/323; 600/310
(58) Field of Classification Search .................. 600/310, 600/323, 331, 340
See application file for complete search history.

(56) References Cited

U.S. PATENT DOCUMENTS

| | | | | |
|---|---|---|---|---|
| 5,372,136 | A | * | 12/1994 | Steuer et al. .................. 600/326 |
| 5,431,170 | A | * | 7/1995 | Mathews ...................... 600/323 |
| 5,588,427 | A | * | 12/1996 | Tien .............................. 600/323 |
| 5,827,182 | A | | 10/1998 | Raley et al. |
| 6,064,898 | A | | 5/2000 | Aldrich |
| 6,360,114 | B1 | | 3/2002 | Diab et al. |
| 6,654,624 | B2 | | 11/2003 | Diab et al. |
| 6,714,803 | B1 | | 3/2004 | Mortz |
| 6,842,635 | B1 | | 1/2005 | Parker |
| 6,882,874 | B2 | * | 4/2005 | Huiku ........................... 600/331 |
| 2002/0042558 | A1 | | 4/2002 | Mendelson |
| 2005/0203357 | A1 | | 9/2005 | Debreczeny et al. |
| 2006/0211925 | A1 | * | 9/2006 | Lamego et al. ............... 600/310 |

* cited by examiner

*Primary Examiner* — Eric Winakur
*Assistant Examiner* — Chu Chuan (JJ) Liu
(74) *Attorney, Agent, or Firm* — Global Patent Operation; Jonathan E. Thomas

(57) ABSTRACT

The invention relates to a probe and a method for use with a probe, which produces signals indicative of the light absorption of arterial blood at least at a first light wave-length and at a second light wavelength. In order to indicate if the probe is not properly attached to a tissue site the method comprises measuring with at a third wave-length. The third wavelength is chosen so that human tissue is less transparent than at the first and second wavelengths.

8 Claims, 1 Drawing Sheet

PROBE AND A METHOD FOR USE WITH A PROBE

BACKGROUND OF THE INVENTION

The invention relates to a method for use with a probe, which produces a signal indicative of the light absorption of arterial blood at least at a first light wave-length and at a second light wavelength. The invention relates further to a probe comprising a light source sending optical signals through the tissue at least at a first light wavelength and at a second light wavelength, and a detector receiving optical signals after transmission through the tissue for producing signals indicative of the light absorption of arterial blood.

The invention relates for example to devices used for non-invasively determining the amount of at least one light absorbing substance in a subject. These devices are typically pulse oximeters used to measure the blood oxygenation of a patient. More specifically, the invention relates to the detection of "probe-off" in such a device. The invention relates generally to devices used for non-invasively determining the amount of at least one light absorbing substance in a subject. These devices are typically pulse oximeters used to measure the blood oxygenation of a patient. More specifically, the invention relates to the detection of "probe-off" in such a device.

Pulse oximetry is at present the standard of care for the continuous monitoring of arterial oxygen saturation ($SpO_2$). Pulse oximeters provide instantaneous in-vivo measurements of arterial oxygenation, and thereby provide early warning of arterial hypoxemia, for example.

A pulse oximeter comprises a computerized measuring unit and a probe attached to the patient, typically to his or her finger or ear lobe. The probe includes a light source for sending an optical signal through the tissue and a photo detector for receiving the signal after transmission through the tissue. On the basis of the transmitted and received signals, light absorption by the tissue can be determined. During each cardiac cycle, light absorption by the tissue varies cyclically. During the diastolic phase, absorption is caused by arterial and venous blood, tissue, bone, and pigments, whereas during the systolic phase, there is an increase in absorption, which is caused by the influx of arterial blood into the tissue. Pulse oximeters focus the measurement on this arterial blood portion by determining the difference between the peak absorption during the systolic phase and the constant absorption during the diastolic phase. Pulse oximetry is thus based on the assumption that the pulsatile component of the absorption is due to arterial blood only.

Light transmission through an ideal absorbing sample is determined by the known Lambert-Beer equation as follows:

$$I_{out}=I_{in}e^{-sDC} \quad (1),$$

where $I_{in}$ is the light intensity entering the sample, $I_{out}$ is the light intensity received from the sample, D is the path length through the sample, $\epsilon$ is the extinction coefficient of the analyte in the sample at a specific wavelength, and C is the concentration of the analyte. When $I_{in}$, D, and $\epsilon$ are known and $I_{out}$ is measured, the concentration C can be calculated.

In pulse oximetry, in order to distinguish between the two species of hemoglobin, oxyhemoglobin ($HbO_2$), and deoxyhemoglobin (RHb), absorption must be measured at two different wavelengths, i.e. the probe includes two different light emitting diodes (LEDs). The wavelength values widely used are 660 nm (red) and 940 nm (infrared), since the said two species of hemoglobin have substantially different absorption values at these wavelengths. Each LED is illuminated in turn at a frequency which is typically several hundred Hz.

The practical functionality of a pulse oximeter is affected by several factors. This is discussed briefly in the following.

First of these is that the finger must be reliably placed in the optical path from LED emitters to the photodetector. If the probe is off, depending of the probe type (clip or wrap) the detection of this condition, just based on the two optical signals, plus a signal proportional to the ambient light, i.e. independent of the LED intensities, is frequently unreliable.

Also conditions where the finger is partly in the optical path, or if coatings such as nail polish are interfering, operation of the oximeter may be erratic, without the system being able to detect this condition.

Furthermore, even with the probe correctly positioned, the optical signal may be degraded by both noise and motion artifacts. One source of noise is the ambient light received by the photodetector. Many solutions have been devised with the aim of minimizing or eliminating the effect of the movement of the patient on the signal, and the ability of a pulse oximeter to function correctly in the presence of patient motion depends on the design of the pulse oximeter. This condition is frequently confused with a probe-off condition, especially with wrap type sensors, where the CTR detection mechanism does not work.

Detecting probe-off in a pulse oximetry sensor is traditionally based on the increase in signal when a clip-on probe has no finger inserted (current transfer ratio CTR above threshold) or, in the case of a flexible or disposable probe, when the signal is noisy or uncorrelated.

Both methods work, but have limitations. The CTR method requires amplitude discriminated LED transmitters, and the correlation method is slower and frequently unreliable.

As examples of the solutions known in the prior art U.S. Pat. Nos. 5,827,182, 6,714,803 and 6,360,114 can be mentioned.

BRIEF DESCRIPTION OF THE INVENTION

An object of the invention is to provide a method and a probe eliminating the disadvantages of the prior art. This is achieved by the method and the probe according to the invention. The method of the invention is characterized in that in order to indicate if the probe is not properly attached to a tissue site the method comprises measuring with at a third wavelength, the third wavelength being chosen so that human tissue is less transparent than at the first and second wavelengths. The probe of the invention is characterized in that in order to indicate if the probe is not properly attached to a tissue site the probe further comprises a light emitter producing a signal at a third wavelength, the third wavelength being chosen so that human tissue is less transparent than at the first and second wavelengths.

The most important advantage of the invention is that the situation in which for example the probe is off is very reliably detected when compared to the prior art. The advantage of the invention is also in that the invention is very simple, and therefore the invention is inexpensive to take into use and to use.

In the following the invention will be described in detail by means of a preferred exemplary embodiment in the accompanying drawing, in which

BRIEF DESCRIPTION OF THE DRAWINGS

FIG. 1 shows schematically a pulse oximeter of the invention. Reference number 1 shows a patient. In the embodiment shown in FIG. 1 measurement is carried out from a finger of the patient, and therefore only one finger of the patient is shown.

DETAILED DESCRIPTION OF THE INVENTION

Figure 1:
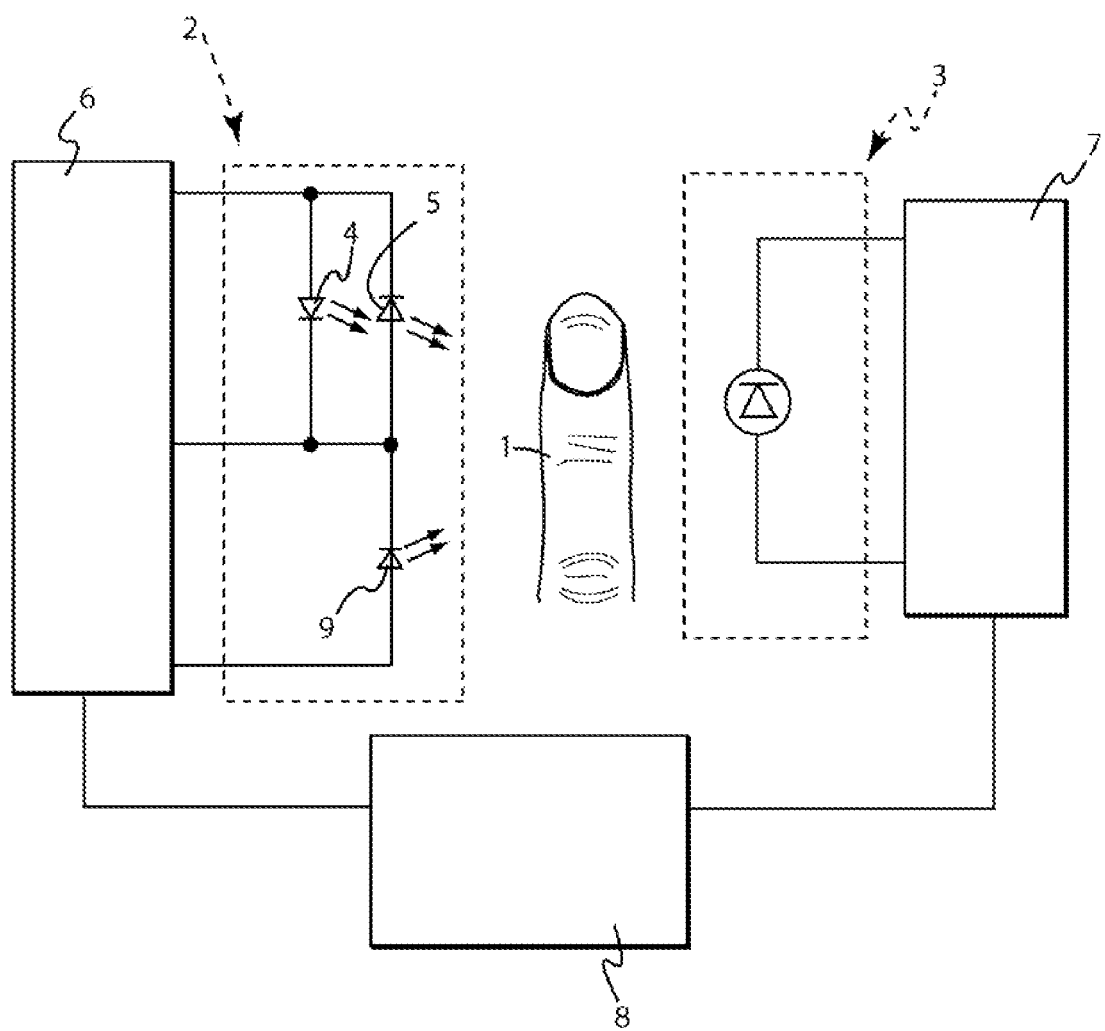
FIG. 1 shows schematically one embodiment of the invention.

Reference number 2 shows a light source and reference number 3 a photo detector. The light source 2 sends optical signals through the tissue at least at a first light wavelength and at a second light wavelength. The detector 3 receives optical signals after transmission through the tissue for producing signals indicative of the light absorption of arterial blood.

In the embodiment shown light source 2 comprises two different light emitting diodes (LED) 4, 5 having wavelengths of 660 nm (red) and 940 nm (infra-red), since the two species of haemoglobin have two substantially different absorption values at these wavelengths as described earlier.

The device comprises further a drive unit 6 for light emitting diodes, an input amplifier 7 for the photo detector 3, and a control unit 8.

The matters described above are known to a person skilled in the art, and therefore said matters are not described in detail here.

The idea in the invention is that in order to indicate if the probe is not properly attached to a tissue site the invention comprises measuring with at a third wavelength, the third wavelength being chosen so that human tissue is less transparent than at the first and second wavelengths. In other words in order to indicate if the probe is not properly attached to a tissue site the probe further comprises a light emitter 9 producing a signal at a third wavelength. The third wavelength is chosen so that it does not penetrate human tissue in the way as the first and the second wavelengths do.

Typically, the red and infrared signals penetrate human tissue in a similar fashion, somewhat dependent of the tissue type, skin color and oxygenation status.

As said above in this invention a third wavelength is added, typically green or blue, that essentially does not penetrate human tissue, or where the tissue absorption is significantly stronger than at the other two wavelengths.

The third wavelength is shorter than 600 nm or longer than 1000 nm. Preferably the third wavelength is essentially 500-550 nm or 1300 nm or more.

The third wavelength can also be a mixture of wavelengths, as in white light, as long as the fraction of the less transparent wavelengths is significant enough to allow identification of the higher absorption in human tissue.

By comparing the CTR of two or more wavelengths, for example the three wavelengths shown in FIG. 1, the system can characterize the type of obstacle, or the lack of obstacle, in the optical path. Thus a clip probe without a finger shows similar CTRs for all three wavelengths (colors), whereas a finger passes red and infrared, but blocks green.

A wrap type probe that is open, i.e. the LEDs do not face the detector, usually has equally low CTRs for all colors, except when it leans onto a blanket or other reflecting object. Again, comparing the three CTRs enables the new system to discriminate a normal reflecting surface from human tissue with much better reliability than just having two wavelengths.

In the embodiment shown only one wavelength not penetrating human tissue is used. This is however not the only possibility but within the spirit of the invention it is quite possible to use also more than one poorly penetrating wavelengths if needed. It is also quite possible to use more than two tissue penetrating wavelengths, i.e. more that red and infrared described in FIG. 1, if there is some need for additional measurements.

The embodiment described above is not intended to restrict the invention, but the invention can be modified quite freely within the scope of the claims enclosed. The details of the invention need not be exactly similar shown for example in FIG. 1 but other solutions can also be used. It is for example quite possible to modify the device shown so that it gives a appropriate alarm if the results obtained show that the probe is not properly attached to a tissue site etc.

What is claimed is:

1. A method comprising:
   determining if a probe capable of producing signals indicative of light absorption of arterial blood at a first light wavelength and at a second light wavelength is not properly attached to a tissue site by measuring with a third light wavelength, which does not penetrate the tissue site as much as the first and second wavelengths; and comparing a current transfer ratio (CTR) of at least one of the first and second light wavelengths with a CTR of the third light wavelength.

2. The method of claim 1, wherein the third light wavelength is shorter than 600 nm or longer than 1000 nm.

3. The method of claim 2, wherein the third light wavelength is about 550-500 nm or 1300 nm or more.

4. The method of claim 1, wherein the probe is a pulse oximeter probe.

5. A probe comprising:
   a light source to send optical signals through tissue at least at a first light wavelength and at a second light wavelength;
   a detector to receive optical signals after transmission of the first and second light wavelengths through the tissue and to produce signals based on the first and second light wavelengths respectively that are indicative of light absorption of arterial blood;
   a light emitter to produce a signal at a third light wavelength to determine if the probe is not properly attached to a tissue site, wherein the third light wavelength does not penetrate the tissue site as much as the first and second light wavelengths; and a unit for comparing a current transfer ratio (CTR) of at least one of the first and second light wavelengths with a CTR of the third light wavelength.

6. The probe of claim 5, wherein the third wavelength is shorter than 600 nm or longer than 1000 nm.

7. The probe of claim 6, wherein the third wavelength is essentially 500-550 nm or 1300 nm or more.

8. The probe of claim 5, wherein the probe is a pulse oximeter probe.

* * * * *